US00PP18393P2

(12) United States Plant Patent
Irie

(10) Patent No.: US PP18,393 P2
(45) Date of Patent: Jan. 1, 2008

(54) ***HYDRANGEA* PLANT NAMED 'RIE 06'**

(50) Latin Name: *Hydrangea macrophylla*
Varietal Denomination: RIE 06

(76) Inventor: Ryoji Irie, 3-7 Narutaki Honmachi Ukyoku, Kyoto (JP)

( * ) Notice: Subject to any disclaimer, the term of this patent is extended or adjusted under 35 U.S.C. 154(b) by 1 day.

(21) Appl. No.: 11/542,030

(22) Filed: Oct. 3, 2006

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell

(57) ABSTRACT

A new cultivar of *Hydrangea* plant named 'RIE 06' that is characterized by broad upright habit, large medium-green leaves, flowers that are dark rose pink in color, and compactness in size. In combination these traits set 'RIE 06' apart from all other existing varieties of *Hydrangea* known to the inventor.

2 Drawing Sheets

Genus: *Hydrangea.* Species: *macrophylla.*
Denomination: 'RIE 06'.

BACKGROUND OF THE INVENTION

The present invention relates to a new and distinct cultivar of *hydrangea* that is grown for use as an indoor floral potted plant and an outdoor ornamental flowering shrub. The new cultivar is known botanically as *Hydrangea macrophylla* and will be referred to hereinafter by the cultivar name 'RIE 06'.

'RIE 06' resulted from a breeding program that was conducted by the inventor at the inventor's nursery in Kyoto, Japan and began in 1990. The purpose of the breeding program was to produce new varieties of floral potted *hydrangeas* that exhibit new and unique flowers and flower color.

Between May 1990 and May 1993 the inventor assembled a collection of unnamed and unreleased hybrids from a sequence of deliberate pollinations involving the following cultivars, all unpatented, and available in commerce in Japan: *Hydrangea macrophylla* 'Otafuku', *Hydrangea macrophylla,* 'Yamaajisai', and *Hydrangea macrophylla* 'Fijinishiritaki'. The inventor did not record which variety was used as male parent and which as female parent. In May 1993, the inventor carried out a deliberate pollination between one unnamed plant from the inventor's collection as female parent and the variety *Hydrangea macrophylla* 'Sumidanohanabi' (unpatented) as male parent.

The pollination described above produced thirty-five individual varieties, which the inventor considered novel and unusual. One of these individual varieties was selected by the inventor in June 1994 and is the subject of the present invention, 'RIE 06'.

'RIE 06' is a deciduous shrub that exhibits large dark-green leaves dark rose pink flowers that bloom in summer. Selection was based on the distinguishing characteristics of flowers, flower color, and inflorescence development. Mop-head type *hydrangeas* produce showy sterile flowers along the outside of the inflorescence, and small inner flowers that are fertile flowers. 'RIE 06' produces numerous sterile flowers. The few fertile flowers that are produced are severely deformed in the bud stage and wither before opening. A mature inflorescence consists of only sterile flowers. 'RIE 06' is distinguishable from the parent plants by flower color, and unique inflorescence development, which produces an average of 275 sterile flowers and 80 fertile flowers per inflorescence. The closest cultivar of *hydrangea* known to the inventor is the inventor's variety *Hydrangea* 'RIE 09' (U.S. Plant Pat. No. 16,613). Whereas 'RIE 06' has only sterile flowers in its mature state, 'RIE 09' bears both sterile flowers and fertile flowers. 'RIE 06' has an average of 19 tepals on the sterile flowers in a deep purplish-pink color; 'RIE 09' has an average of 14 tepals on the sterile flowers in a lighter pink color.

'RIE 06' was first asexually propagated by the inventor in the spring of 1995 in a cultivated area of Kyoto, Japan. The method used for asexual propagation was softwood cuttings. The characteristics of the new *Hydrangea* cultivar named 'RIE 06' have been determined stable and are reproduced true to type in successive generations.

SUMMARY OF THE INVENTION

The following traits have been repeatedly observed and represent the characteristics of the new *Hydrangea* cultivar 'RIE 06'. These traits in combination distinguish 'RIE 06' from all other commercial varieties of *Hydrangea* known to the inventor. 'RIE 06' has not been tested under all possible conditions and phenotypic differences may be observed with variations in environmental, climatic and cultural conditions, without however, any difference in genotype.

1. *Hydrangea* 'RIE 06' is grown for use as both an indoor floral potted plant and an outdoor ornamental flowering shrub.
2. *Hydrangea* 'RIE 06' exhibits flowers that are dark rose pink.
3. *Hydrangea* 'RIE 06' exhibits unique inflorescence development that produces an average of 275 sterile flowers and 80 deformed fertile flowers per inflorescence.
4. *Hydrangea* 'RIE 06' exhibits a broad upright habit.
5. *Hydrangea* 'RIE 06' exhibits large medium green leaves.

6. *Hydrangea* 'RIE 06' is 25 cm in height and 33.5 cm in diameter in a 1.5-liter container.
7. *Hydrangea* 'RIE 06' is a shrub.
8. *Hydrangea* 'RIE 06' is deciduous.
9. *Hydrangea* 'RIE 06' performs best when planted in loam based moisture retentive soil, in partial shade, with regular water.
10. *Hydrangea* 'RIE 06' is asexually propagated by the method of softwood cuttings.
11. *Hydrangea* 'RIE 06' exhibits rigid, strong basal branches.
12. *Hydrangea* 'RIE 06' is hardy to USDA Zone 5.
13. *Hydrangea* 'RIE 06' blooms continuously from early April to September.

BRIEF DESCRIPTION OF THE DRAWINGS

The accompanying color drawings illustrate the overall appearance of the new *Hydrangea* cultivar 'RIE 06' showing the colors as true as it is reasonably possible to obtain in colored reproductions of this type. Colors in the photographs may differ from the color values cited in the detailed botanical description, which accurately describe the actual colors of the new variety of *Hydrangea* named 'RIE 06'.

The drawing labeled as FIG. 1 depicts an individual whole plant growing in a 1.5-liter container in a frost-protected greenhouse in De Kwakel, The Netherlands. The plant is approximately twenty one months old. The plant was produced from a cutting which was rooted and grown in a four inch container, then transplanted into the 1.5 liter container and allowed to flower in its natural season.

The drawing labeled

Figure 1:
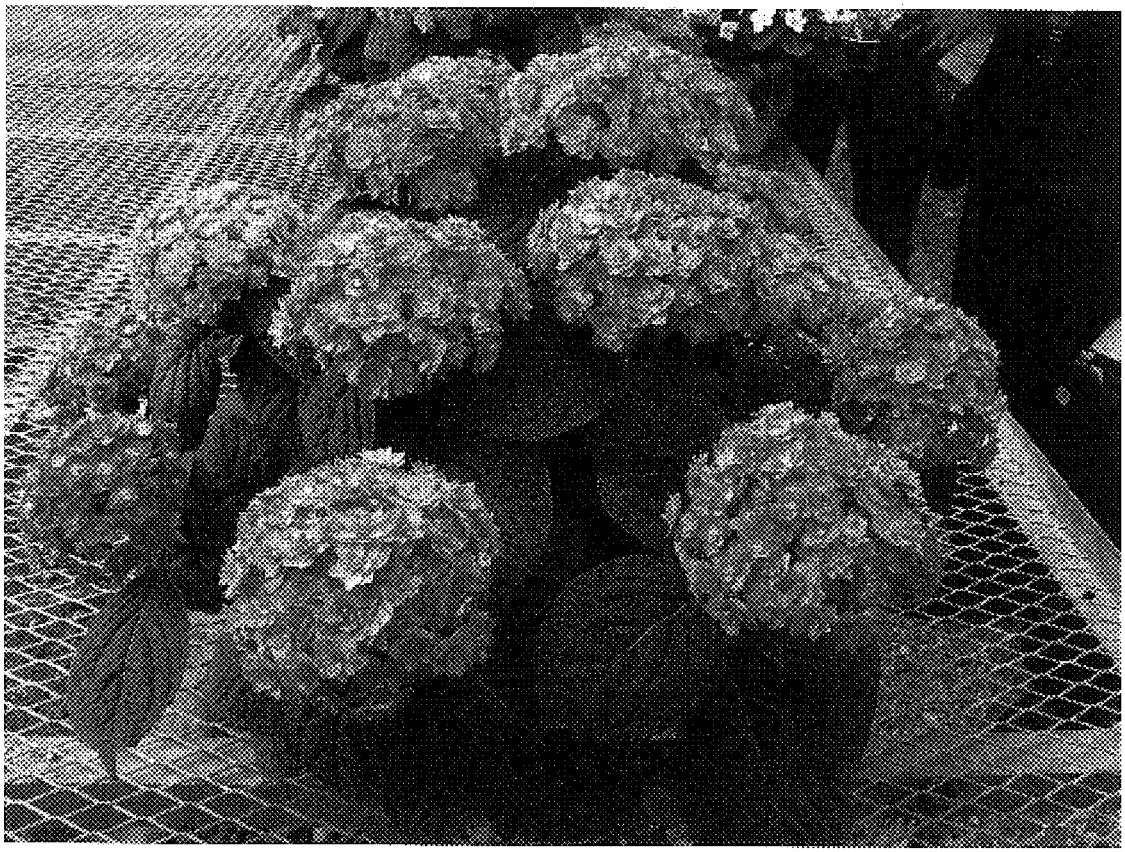
Figure 2:
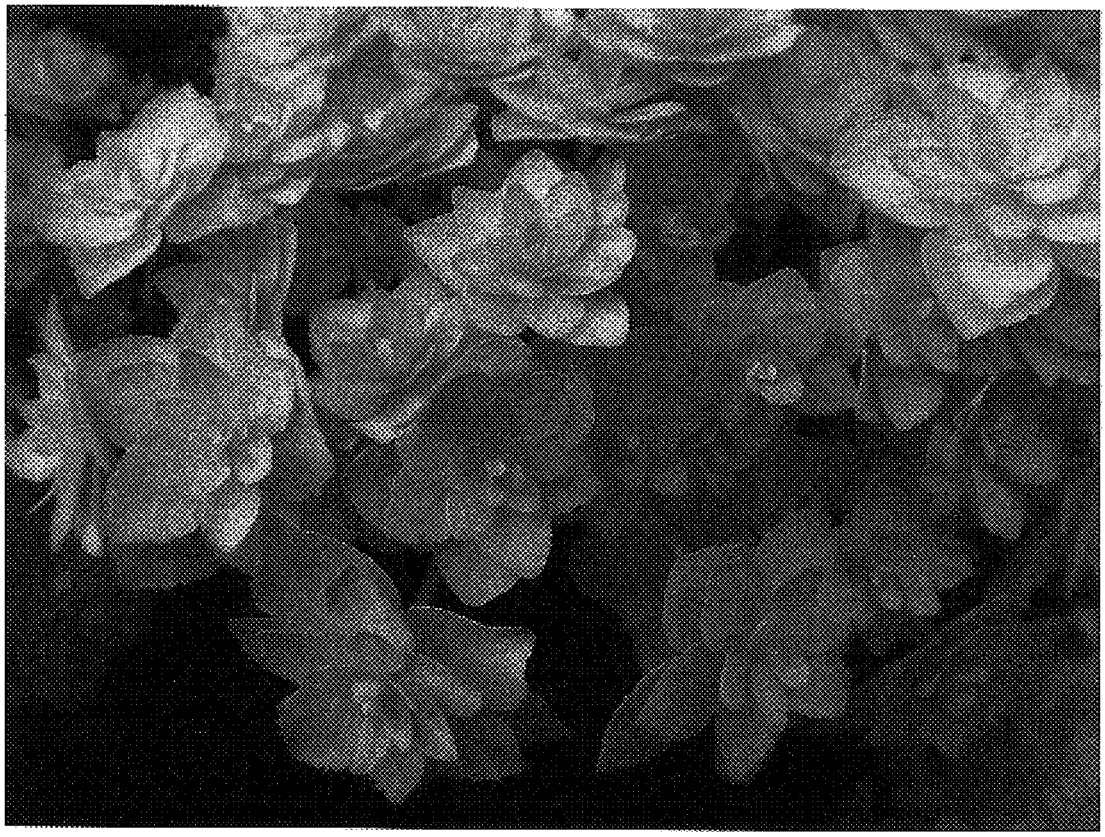
FIG. 2 illustrates a portion of the inflorescence of 'RIE 06' with a close-up view of the sterile flowers.

All drawings were made using conventional techniques and although colors may appear different from actual colors due to light reflectance they are as accurate as possible, by conventional photography.

BOTANICAL DESCRIPTION OF THE PLANT

The following is the detailed description of 'RIE 06' as grown in a greenhouse in De Kwakel, The Netherlands. Data was collected in June 2006 from 12-month-old plants grown in 1.5-liter containers. The color determinations are in accordance with the 2001 Edition of the Colour Chart of The Royal Horticultural Society, London, England, except where general color terms of ordinary dictionary significance are used. The growing requirements are similar to the species.

Botanical classification: *Hydrangea macrophylla* 'RIE 06'.
Genus: *Hydrangea.*
Species: *macrophylla.*
Denomination: 'RIE 06'.
Commercial classification: Floral plant, ornamental shrub.
Common name: *Hydrangea.*
Use: Grown for use as a potted indoor plant or as an outdoor ornamental flowering shrub.
Container size: Suggested container size is 1.5-liter.
Cultural requirements: Performs best when planted in loam based moisture retentive soil, in partial shade, with regular water.
Parentage: *Hydrangea macrophylla* 'RIE 06' is a hybrid plant that resulted from the induced cross-pollination of the following parent plants:

*Female parent.*—An unnamed individual *Hydrangea macrophylla.*
*Male parent.*—An individual *Hydrangea macrophylla* 'Sumidanohanabi' (unpatented).

Plant description:
*Blooming seasons.*—Spring and summer (natural season) or year-round if forced.
*Plant habit.*—Broad upright.
*Plant type.*—Deciduous shrub.
*Overall plant shape.*—Broad inverted triangle.
*Vigor.*—Moderate.
*Growth rate.*—An average of 10-cm per month in spring.
*Plant height.*—25 cm in height.
*Plant diameter.*—33.5 cm in diameter.
*Hardiness.*—USDA Zone 5.
*High temperature tolerance.*—Tolerant to 32° Centigrade.
*Root system.*—Fibrous.
*Propagation.*—Propagation is accomplished by the method of softwood cuttings.
*Time and temperatures to develop roots.*—Approximately 4 weeks is needed to develop roots on an initial cutting, at temperatures of 18° to 20° Centigrade.
*Crop time* (*outdoor plant crop*).—An average of 12 months is needed to produce a commercial container size flowering outdoor plant, from a rooted cutting.
*Temperature* (*outdoor plant crop*).—From rooted cuttings to commercial size containers, the outdoor crop is grown at natural outdoor temperatures utilizing unheated greenhouses for winter protection.
*Crop time* (*indoor plant crop*).—An average of 4–6 months is needed to produce a commercial container size flowering indoor plant, from a rooted cutting.
*Temperatures* (*indoor plant crop*).—Transplant rooted cuttings to liner pots and keep for a minimum of 6 weeks at below 5° Centigrade to force dormancy. Transplant to 1.5-liter containers and keep at 18° to 25° Centigrade for a minimum of 10 weeks to produce commercial container size flowering plants.
*Disease and pest resistance or susceptibility.*—No susceptibility to pests or disease known to the inventor.

Stem:
*Number of lateral branches.*—An average of 6 lateral branches.
*Lateral branch length.*—Average is 12.2 cm in length.
*Lateral branch diameter.*—Average is 5 mm in diameter.
*Stem shape.*—Rounded.
*Stem surface.*—Slightly glossy.
*Pubescence.*—None observed.
*Stem strength.*—Strong.
*Stem texture.*—Rigid.
*Stem color.*—Individual colors 144A and 144B at the nodes; stems are N186B and N186C.
*Lenticels.*—Present. Quantity: An average of 14 per cubic cm of stem surface. Dimensions: An average of 1 mm in length and 0.5 mm in width. Color: N186B and N186C.
*Branching habit.*—Moderate branching.
*Basal branching.*—No, but can occur due to pinching.
*Branching requirements.*—Pinching encourages lateral branching.
*Internode length.*—6.5 cm between nodes.

Foliage:

*Type.*—Deciduous.

*Arrangement.*—Opposite.

*Division.*—Simple.

*Quantity of leaves per lateral stem.*—An average of 10 (5 pairs).

*Leaves.*—Dimensions: An average of 10.8 cm in length and 7.7 cm in width. Shape: Broad elliptic. Tip: Apiculate. Base: Obtuse. Margin: Crenate. Texture: Smooth, only slightly glossy. Pubescence: None observed. Color, immature (adaxial): 137A. Color, immature (abaxial): 137C and 138A. Color, mature (adaxial): In between 139A and 147A. Color, mature (abaxial): N138B.

*Venation pattern.*—Pinnate.

*Vein color* (*adaxial*).—143C.

*Vein color* (*abaxial*).—144D and 145B.

*Attachment.*—Petiole.

*Petiole dimensions.*—An average of 1.8 cm in length and 3 mm in diameter.

*Petiole color.*—144A and 144B.

*Durability of foliage to stress.*—High.

*Stipules, tendrils, thorns, spines, or prickles.*—None.

*Fragrance.*—None observed.

Flowers:

*Flower arrangement.*—Terminal inflorescence.

*Inflorescence type.*—Compound corymb.

*Inflorescence dimensions.*—An average of 7.4 cm in height and 11.6 cm in diameter.

*Quantity of flowers per inflorescence.*—An average of 275 sterile flowers and 80 strongly deformed fertile flowers.

*Flowering habit.*—Summer.

*Quantity of flowers and buds per plant.*—An average of 1650 sterile buds and flowers, and an average of 480 deformed fertile buds which wither before developing before flowering per individual plant.

*Rate of opening* (*fertile and sterile flowers*).—An average of 10% of the sterile flowers open at any stage; all opened in approximately 6 weeks.

*Fragrance.*—None.

*Bud.*—Dimensions, sterile flower: An average of 6 mm in length and 5 mm in width. Dimensions, fertile flower: An average of 2 mm in length and 1.5 mm in width. Shape: Ovate. Color: 145C and 145D. Rate of opening: Sterile flowers open approximately 1 week after bud-stage. Fertile flowers are strongly deformed and do not open, but wither after bud-stage.

*Flower aspect.*—Dropping to outward to upright.

*Flower shape.*—Rotate.

*Peduncle.*—Dimensions: An average of 3.6 cm in length and 3 mm in width. Angle: An average of 60° (0°=straight upright). Strength: Strong. Color: 145D and 150D. Lenticels: Present Lenticel dimensions: An average of 0.75 mm in length and 0.3 mm in width.

*Pedicel.*—Dimensions: An average of 2.6 cm in length and 1 mm in diameter. Average angle: 50° Strength: Moderate. Color: 63B.

*Sterile flowers.*—Tepal dimensions: An average of 1.4 cm in length and 1.1 cm in width. Tepal number: An average of 19. Tepal appearance: Dull. Tepal texture: Smooth. Tepal arrangement: Rotate. Fused or unfused: Unfused. Tepal shape: Rhomboidal to elliptic. Tepal margin: Crenate. Tepal tip: Bluntly acute. Tepal color, when opening (adaxial): 62C and 62D. Tepal color, when opening (abaxial): 62D. Tepal color, fully opened (adaxial): 68B and 68C. Tepal color, fully opened (abaxial): 62C with 62B margins. Sepals: No sepals, sterile flowers have no calyx but consist of tepals only. Calyx: None.

*Fertile flowers.*—None present; wither after bud-stage.

*Flower fragrance.*—None observed.

Reproductive organs: None, fertile flowers wither after bud-stage.

Seed production: No seed production has been observed to date.

It is claimed:

1. A new and distinct cultivar of *Hydrangea* plant named 'RIE 06' as described and illustrated herein.

* * * * *